(12) United States Patent
Das et al.

(10) Patent No.: US 11,129,404 B2
(45) Date of Patent: Sep. 28, 2021

(54) NUTRITIONAL COMPOSITIONS COMPRISING HYDROLYZED PROTEIN AND A MODIFIED FAT SYSTEM AND USES THEREOF

(71) Applicant: ABBOTT LABORATORIES, Abbott Park, IL (US)

(72) Inventors: Tapas Das, Worthington, OH (US); Mustafa Vurma, Dublin, OH (US); Chron-Si Lai, Blacklick, OH (US); Paul Johns, Columbus, OH (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 16/066,585

(22) PCT Filed: Dec. 27, 2016

(86) PCT No.: PCT/US2016/068701
§ 371 (c)(1),
(2) Date: Jun. 27, 2018

(87) PCT Pub. No.: WO2017/117121
PCT Pub. Date: Jul. 6, 2017

(65) Prior Publication Data
US 2019/0014807 A1      Jan. 17, 2019

Related U.S. Application Data

(60) Provisional application No. 62/271,644, filed on Dec. 28, 2015.

(51) Int. Cl.
| | |
|---|---|
| *A23L 33/00* | (2016.01) |
| *A61K 38/01* | (2006.01) |
| *A23L 33/12* | (2016.01) |
| *A23L 33/19* | (2016.01) |
| *A23L 33/18* | (2016.01) |
| *A23L 33/115* | (2016.01) |
| *A61K 45/06* | (2006.01) |
| *A23L 29/00* | (2016.01) |
| *A61P 25/28* | (2006.01) |
| *A23L 33/125* | (2016.01) |
| *A61K 31/575* | (2006.01) |
| *A61K 31/685* | (2006.01) |

(52) U.S. Cl.
CPC ............. *A23L 33/40* (2016.08); *A23L 29/035* (2016.08); *A23L 33/115* (2016.08); *A23L 33/12* (2016.08); *A23L 33/18* (2016.08); *A23L 33/19* (2016.08); *A61K 38/018* (2013.01); *A61K 45/06* (2013.01); *A61P 25/28* (2018.01); *A23L 33/125* (2016.08); *A23V 2002/00* (2013.01); *A23V 2200/322* (2013.01); *A23V 2250/186* (2013.01); *A23V 2250/1842* (2013.01); *A23V 2250/192* (2013.01); *A23V 2250/30* (2013.01); *A23V 2250/54246* (2013.01); *A23V 2250/54252* (2013.01); *A61K 31/575* (2013.01); *A61K 31/685* (2013.01); *A61K 2300/00* (2013.01)

(58) Field of Classification Search
None
See application file for complete search history.

(56) References Cited

U.S. PATENT DOCUMENTS

| | | |
|---|---|---|
| 5,292,538 A | 3/1994 | Paul et al. |
| 5,480,872 A | 1/1996 | Cope et al. |
| 5,547,687 A | 8/1996 | Outinen et al. |
| 7,261,911 B2 | 8/2007 | Luebbers |
| 7,297,354 B2 | 11/2007 | Miller et al. |
| 7,682,625 B2 | 3/2010 | Gans |
| 7,838,004 B2 | 11/2010 | Mower |
| 7,972,808 B2 | 7/2011 | Edens et al. |
| 8,273,710 B2 | 9/2012 | Boots |
| 8,377,496 B2 | 2/2013 | Clinger et al. |
| 8,431,531 B2 | 4/2013 | Boots |
| 8,889,233 B1 | 11/2014 | Kelman et al. |
| 8,932,651 B2 | 1/2015 | Lax et al. |
| 2006/0106226 A1 | 5/2006 | Pollack et al. |
| 2006/0210697 A1 | 9/2006 | Mower |
| 2008/0161227 A1 | 7/2008 | Roos et al. |
| 2009/0075904 A1* | 3/2009 | Boots ............... A61K 38/018 514/1.1 |
| 2009/0162518 A1 | 6/2009 | Clinger et al. |
| 2009/0186098 A1 | 7/2009 | Briceno |

(Continued)

FOREIGN PATENT DOCUMENTS

| | | |
|---|---|---|
| EP | 2 725 105 A1 | 4/2014 |
| JP | 2016000601 A | 1/2016 |

(Continued)

OTHER PUBLICATIONS

Invitation to Pay Additional Fees from PCT/US2016/068701 dated Apr. 21, 2017.
International Search Report and Written Opinion from PCT/US2016/068701 dated Jun. 13, 2017.
Invitation to Pay Additional Fees from PCT/US2016/068669 dated Mar. 13, 2017.

(Continued)

*Primary Examiner* — Christina Bradley
(74) *Attorney, Agent, or Firm* — Calfee, Halter & Griswold LLP

(57) ABSTRACT

Disclosed embodiments provide nutritional compositions and methods of enhancing maturation of an infant's brain. The methods include the step of administering to the infant a nutritional composition comprising a protein with a degree of hydrolysis of 10% to 75% in combination with at least one of a monoglyceride, a free fatty acid, a salt of a free fatty acid, a phospholipid, and cholesterol.

13 Claims, 7 Drawing Sheets

(56) References Cited

U.S. PATENT DOCUMENTS

| | | |
|---|---|---|
| 2009/0297689 A1 | 12/2009 | Edens et al. |
| 2011/0039768 A1 | 2/2011 | Rochelle et al. |
| 2011/0091440 A1 | 4/2011 | Sabin |
| 2012/0171350 A1* | 7/2012 | Lai .................. A23L 33/30 426/611 |
| 2013/0096074 A1 | 4/2013 | Boots |
| 2013/0331315 A1 | 12/2013 | Krul et al. |
| 2014/0107193 A1* | 4/2014 | Kuang .................. A61K 31/353 514/456 |
| 2014/0271586 A1 | 9/2014 | Hondmann et al. |
| 2014/0271979 A1 | 9/2014 | Ao et al. |
| 2015/0018282 A1 | 1/2015 | Lang et al. |
| 2015/0093463 A1 | 4/2015 | Hondmann et al. |
| 2015/0189905 A1 | 7/2015 | Banavara et al. |

FOREIGN PATENT DOCUMENTS

| | | |
|---|---|---|
| WO | 2003011055 | 2/2003 |
| WO | 2006068480 A2 | 5/2006 |
| WO | 2006099013 A2 | 9/2006 |
| WO | 2007064208 A1 | 6/2007 |
| WO | 2008047243 A2 | 4/2008 |
| WO | 2011115476 A1 | 9/2011 |
| WO | 2014160150 A1 | 10/2014 |
| WO | 2015017073 A1 | 2/2015 |
| WO | 2015071401 A1 | 5/2015 |

OTHER PUBLICATIONS

International Search Report and Written Opinion from PCT/US2016/068669 dated May 8, 2017.

Ahmed, "A review of meat protein hydrolysates and hypertension". Meat Science, 86 2010, pp. 110-118.

Harnedy, "In vitro assessment of the cardioprotective, anti-diabetic and antioxidant potential of Palmaria palmata protein hydrolysates." Journal of Applied Phycology, Dec. 2013, vol. 25, Issue 6, pp. 1793-1803.

Journel, Brain Responses to High-Protein Diets Advances in Nutrition, vol. 3, Issue 3, May 1, 2012, pp. 322-329.

Liu et al., Effect of enzymatic hydrolyzed animal protein extracted from pinctada martensii and taurine on brain monoamine neurotransmitters of exhausted mice, 2010, Issue 3, pp. 23-25 (English Abstract Only).

McGregor, "Milk protein for improved metabolic health: a review of the evidence." Nutrition & Metabolism 2013, pp. 1-13.

Nongonierma, "Dipeptidyl peptidase IV inhibitory properties of a whey protein hydrolysate: Influence of fractionation, stability to simulated gastrointestinal digestion and food-drug interaction". Ineternational Dairy Journal 32, 2013, pp. 33-39.

Reidy et al., "Soy-dairy protein blend and whey protein ingestion after resistance exercise increases amino acid transport and transporter expression in human skeletal muscle". Journal of Applied Physiology, Jun. 1, 2014; 116(11):1353-1364.

Reimer, Meat hydrolysate and essential amino acid induced GLP-2 secretion, in the human NCI-H716 enteroendocrine cell line, is regulatd by extracellular signal-regulated kinase 1/2 and p38 mitogen-activeated protein kinases, Journal of Endocrinology 2006 191, pp. 159-170.

Vasilevskaia, "Effect of parenterally administered amino acids and protein hydrolysate on the electrical activity of brain structures" Apr. 1979;65(4):500-6 (English Abstract).

Vutskits, "Celbral Blood Flow in the Neonate" Paediatric Aaesthesia, vol. 24, No. 1, Nov. 15, 2013 pp. 22-29.

\* cited by examiner

BM protect the hypoxia treated pups from brain inflammation
(Frontal Cortex / Corpus Callosum)

B232  Breast Fed Control

B239  NEC Formula

Highly hydrolyzed protein based HMF reduces hypoxia treated mouse brain inflammation

B249  NEC Formula + PDF fortifier

B241  NEC Formula + Control Fortifier ated entry of International Application No. PCT/US2016/068701 filed Dec. 27, 2016, which claims priority to and the benefit of U.S. Provisional Application No. 62/271,644, filed on Dec. 28, 2015, the entire contents of which are incorporated herein by reference.

NUTRITIONAL COMPOSITIONS COMPRISING HYDROLYZED PROTEIN AND A MODIFIED FAT SYSTEM AND USES THEREOF

CROSS REFERENCE TO RELATED APPLICATIONS

This application is the U.S. national stage entry of International Application No. PCT/US2016/068701 filed Dec. 27, 2016, which claims priority to and the benefit of U.S. Provisional Application No. 62/271,644, filed on Dec. 28, 2015, the entire contents of which are incorporated herein by reference.

FIELD

The present disclosure relates to infant nutrition. In particular, the disclosure relates to nutritional compositions and administration of nutritional compositions for enhancing infant brain development.

BACKGROUND

Maturation of the central nervous system, including the brain, is a key developmental area for all newborn infants. Infants born preterm are in a more precarious developmental state as they also are in need of catch-up growth in other areas. Further, preterm infants have a variety of specific nutritional and medical needs such as complications arising from immaturity of organs including the brain. Many of these complications arise from incomplete nutritional absorption and the build-up of by-products that are the result of growth and maturation. Often these complications result in an increased oxidative status in the infant and can further slow development.

SUMMARY

The present disclosure relates to nutritional compositions and methods of enhancing maturation of the brain of an infant. Applicants have found that administration of a nutritional composition comprising particular hydrolyzed proteins in combination with a particular fat system provides unexpected nutritional and health benefits to infants, especially preterm infants and those in need of catch-up growth or development. In particular, blood flow to the brain can be enhanced. Increased blood flow, especially for preterm infants or those in need of catch-up growth, leads to improved development of the brain.

In a first exemplary embodiment, a method of inhibiting neuronal cell death is provided. The method comprises administering to an individual in need thereof a nutritional composition comprising a protein with a degree of hydrolysis of 10% to 75% and at least one of a monoglyceride, a free fatty acid, a salt of a free fatty acid, a phospholipid, and cholesterol. After administration, the individual's neuronal cell death is reduced.

In a second exemplary embodiment, a method of treating neuronal tissue inflammation in an individual in need thereof is provided. The method comprises administering to the individual a nutritional composition comprising a protein with a degree of hydrolysis of 10% to 75% and at least one of a monoglyceride, a free fatty acid, a salt of a free fatty acid, a phospholipid and cholesterol, and wherein after administration the individual's neuronal tissue inflammation is reduced.

In a third exemplary embodiment, a method for the prevention, delay of progression, or the treatment of a neurodegenerative disorder is provided. The method comprises administering, to an individual in need thereof, a nutritional composition comprising a therapeutically effective amount of a dipeptidyl peptidase-4 (PPP-TV) inhibiting protein.

DETAILED DESCRIPTION

Figure 1:
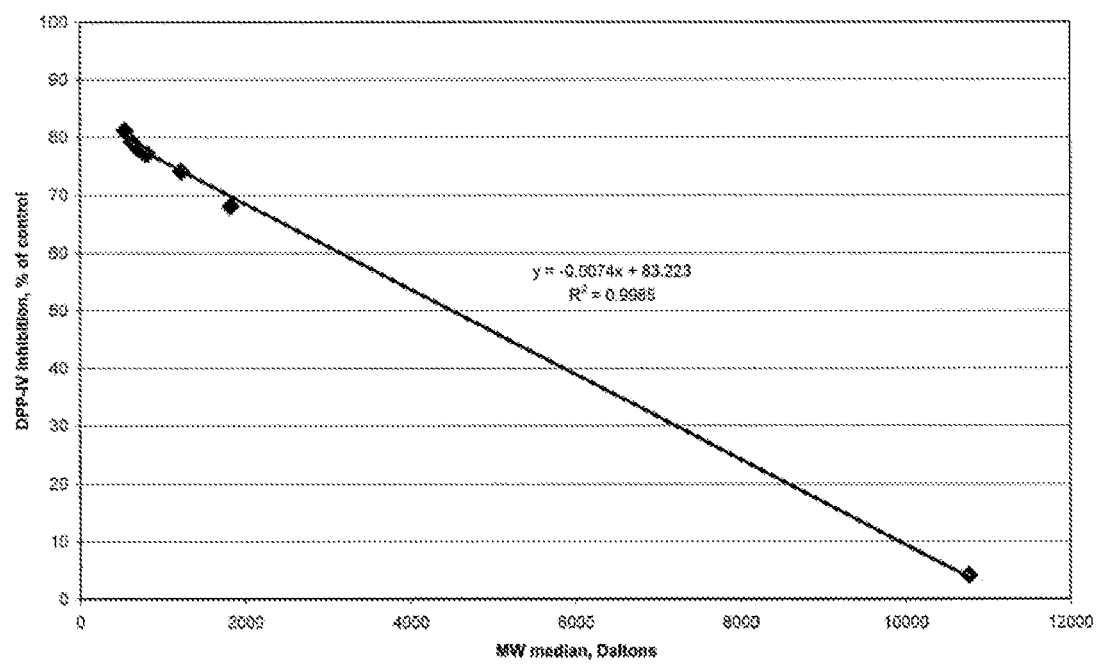
FIG. 1 shows the results of DPP-IV inhibition as a function of molecular weight for several exemplary proteins.

The general inventive concepts will be further described hereinafter in detail with reference to the accompanying drawings and various exemplary embodiments. One of ordinary skill in the art will appreciate that these exemplary embodiments only constitute a fraction of the possible embodiments encompassed by the general inventive concepts. As such, the scope of the present disclosure is by no means limited to the exemplary embodiments set forth herein.

Pre-term infants are born with different levels of maturation and widely varying nutritional needs. In order to meet the individual pre-term infant nutritional needs, it is a common practice to add a nutritional supplement (e.g., human milk fortifier) to either formula or breast milk to produce a diet that provides targeted, enhanced nutrient delivery for the developing infant's sensitive systems.

The general inventive concepts are directed to nutritional compositions including hydrolyzed proteins in combination with a fat system. Applicants have found that, through the inclusion of a protein with a degree of hydrolysis of 10% to 75% and at least one of a monoglyceride, a free fatty acid, a salt of a free fatty acid, a phospholipid, and cholesterol, blood flow can be improved. In addition, glucagon-like peptide 2 (GLP-2) levels are increased. This combination leads to better blood flow, reduced inflammation, and enhanced maturation (e.g., catch-up growth) for an infant, especially a preterm infant.

The enhanced blood flow can benefit the infant in a number of ways. In particular, administration of the nutritional compositions, according to exemplary embodiments described herein, can reduce a level of dipeptidyl peptidase-4 (DPP-IV), which improves brain maturation and development as indicated by measuring, for example, brain cell apoptosis (reduction thereof). Without intending to be limited by theory, it is believed that the particular hydrolyzed protein in combination with at least one of a monoglyceride, a free fatty acid, a salt of a free fatty acid, a phospholipid, and cholesterol, as provided herein, up-regulates the expression of genes that promote blood flow, stimulating brain development via an increasing supply of nutrients and alleviating inflammation.

The nutritional compositions disclosed herein provide the required nutritional benefits for growth and maturation to the infant, while providing the infant with the additional significant advantages of improved blood flow, reduced inflammation, improved brain development, and allowing more aggressive enteral nutritional feeding so that a preterm infant catches up on growth. The nutritional compositions as described herein may provide an individual, such as an infant, with dependable, high quality nutrition, as well as program the infant early in life such that the infant has a head start to improved brain development and improved general overall health later in life. The nutritional compositions as described herein may provide the infant with nutritional benefits early in life that transcend into significant health benefits later in life, allowing the infant potentially to lead a longer, healthier life as a teenager and adult.

These and other features of the nutritional compositions and methods of the present disclosure, as well as some of the many other optional variations and additions, are described in detail hereafter.

The term "nutritional composition," unless otherwise specified, refers to nutritional liquids, nutritional powders, nutritional solids, nutritional semi-liquids, semi-solids, nutritional supplements, nutritional tablets, and any other nutritional food product as known in the art. The nutritional powders may be reconstituted to form a nutritional liquid, all of which comprise one or more of fat, protein and carbohydrate, and are suitable for oral consumption by a human.

The term "nutritional liquid," as used herein, unless otherwise specified, refers to nutritional compositions in ready-to-drink liquid form, concentrated form, and nutritional liquids made by reconstituting the nutritional powders described herein prior to use.

The term "nutritional powder," as used herein, unless otherwise specified, refers to nutritional compositions in flowable or scoopable form that can be reconstituted with water or another aqueous liquid prior to consumption and includes both spray dried and drymixed/dryblended powders.

The term "nutritional semi-solid," as used herein, unless otherwise specified, refers to nutritional compositions that are intermediate in properties, such as rigidity, between solids and liquids. Some semi-solids examples include puddings, gelatins, and doughs.

The term "nutritional semi-liquid," as used herein, unless otherwise specified, refers to nutritional compositions that are intermediate in properties, such as flow properties, between liquids and solids. Some semi-liquids examples include thick shakes and liquid gels.

The terms "hydrolyzed protein" or "protein hydrolysate" as used herein, unless otherwise specified, refer to a source of protein which has been subjected to a specific treatment whose primary purpose is to hydrolyze proteins. In this regard, it is conventional in this industry to refer to a protein source which has been subjected to a treatment whose primary purpose is to hydrolyze intact (or native) proteins to form hydrolyzed proteins, e.g., "whey protein hydrolysate." In contrast, when a protein source has not been subjected to such a treatment, it is conventional practice to refer to this composition as a source of intact protein, or, more commonly, to say nothing about the hydrolysis of its protein.

One way of referring to the extent of hydrolysis of a hydrolyzed protein is by noting its Degree of Hydrolysis (DH). A protein with a DH value of, for example, 30 refers to protein in which 30% of the total peptide bonds within the protein are hydrolyzed (or that 30% of the protein's peptide bonds have been cleaved; e.g., if the intact protein contains 100 peptide bonds, and if 30 of these bonds are cleaved by the hydrolysis process, then the DH of the protein after hydrolysis is 30). As used herein, the degree of hydrolysis generally refers to the amount of amino nitrogen/total nitrogen in the protein.

The term "fat system" as used herein, unless otherwise specified, refers to a portion of the overall fat in a nutritional composition. While certain components of the fat system are not technically fats or fatty acids, the fat system comprises ingredients that are generally associated with the fat or lipid component of a nutritional composition. Further, while the term fat system is used to refer to the these components, those of skill in the art will recognize that certain other ingredients of the nutritional composition may also contribute one or more of the components of the fat system as an inherent portion of the particular ingredient (e.g., certain proteins also include inherent fat or fatty acids). In certain exemplary embodiments, the term refers to the combination of a phospholipid, cholesterol, and at least one of a monoglyceride, a free fatty acid, and a salt of a free fatty acid. In certain exemplary embodiments, the term refers to the combination of a phospholipid, cholesterol, a monoglyceride, and at least one of a free fatty acid and a salt of a free fatty acid. In certain exemplary embodiments, the fat system includes soy lecithin, cholesterol, monoglycerol palmitate and at least one of a free fatty acid from soy and a salt of a free fatty acid from soy.

The term "infant" as used herein, unless otherwise specified, refers to individuals up to 36 months of age, actual or corrected. In certain embodiments, the term "infant" refers to individuals up to 36 months of age, actual or corrected, including individuals up to 12 months of age. The term "preterm infant," as used herein, refers to an infant born prior to 36 weeks of gestation. The term "term infant," as used herein, refers to an infant born at or after 36 weeks of gestation. The term "newborn infant," as used herein, unless otherwise specified, refers to infants less than about 3 months of age, including infants from zero to about 2 weeks of age. The terms "infant" and "newborn infant" include both term and preterm infants.

The term "infant formula," as used herein, unless otherwise specified, refers to liquid and solid nutritional compositions suitable for consumption by an infant. Unless otherwise specified herein, the term "infant formula" is intended to encompass term formulas, preterm infant formulas, and human milk fortifiers.

The term "preterm infant formula," as used herein, unless otherwise specified, refers to liquid and solid nutritional compositions suitable for consumption by a preterm infant.

The terms "susceptible to," and "at risk of," as used herein, are used interchangeably to refer to individuals having little resistance to a certain condition or disease, including being genetically predisposed, having a family history of, and/or having symptoms of the condition or disease. In certain exemplary embodiments, the terms refer to a premature infant or an individual in need of catch-up growth. The terms are intended to refer to an individual with a greater need or are at an increased risk as compared to the general population or subset thereof.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

Product Form

The nutritional compositions of the present disclosure may be formulated and administered in any known or otherwise suitable oral product form. Any solid, liquid, semi-solid, semi-liquid or powder form, including combinations or variations thereof, are suitable for use herein, provided that such forms allow for safe and effective oral delivery to the individual of the essential ingredients as also defined herein.

Specific non-limiting examples of product forms suitable for use with products and methods disclosed herein include, for example, liquid and powder preterm infant formulas, liquid and powder infant formulas, liquid and powder elemental and semi-elemental formulas, and liquid and powder human milk fortifiers.

The nutritional compositions may be formulated with sufficient kinds and amounts of nutrients to provide a sole, primary, or supplemental source of nutrition, or to provide a specialized nutritional composition for use in individuals such as infants afflicted with specific diseases or conditions or with a targeted nutritional benefit.

Desirably, the nutritional compositions include infant formulas formulated for both term and preterm infants. Desirably, the infant formula is formulated for feeding to infants within the first few days, weeks, or months following birth, and including for feeding to infants from age zero to one year, including zero to six months, including zero to four months, and including zero to two months. In some embodiments, the infant formulas are for feeding to newborn infants in the first few weeks of life, including birth to four weeks of life, including birth to three weeks of life, including birth to two weeks of life, and including birth to the first week of life. It is to be understood that the administration of the infant formulas of the present disclosure is not limited to administration during only the first six months following birth, but may be administered to older infants as well.

Nutritional Liquids

Nutritional liquids include both concentrated and ready-to-feed nutritional liquids. These nutritional liquids include liquids formulated as suspensions, emulsions or clear or substantially clear liquids.

Nutritional emulsions suitable for use include aqueous emulsions comprising proteins, fats, and carbohydrates. These emulsions are generally flowable or drinkable liquids at from about 1° C. to about 25° C. and may be in the form of oil-in-water, water-in-oil, or complex aqueous emulsions, although such emulsions are most typically in the form of oil-in-water emulsions having a continuous aqueous phase and a discontinuous oil phase.

The nutritional liquids include liquids which are shelf stable. The nutritional liquids include liquids which contain up to about 95% by weight of water, including from about 50% to about 95%, also including from about 60% to about 90%, and also including from about 70% to about 85%, of water by weight of the nutritional liquid.

Although the serving size for the nutritional liquid can vary depending upon a number of variables, a typical serving sizes include those which are at least about 2 mL, or even at least about 5 mL, or even at least about 10 mL, or even at least about 25 mL, including ranges from about 2 mL to about 300 mL, including from about 100 mL to about 300 mL, from about 4 mL to about 250 mL, from about 150 mL to about 250 mL, and from about 10 mL to about 240 mL.

The nutritional emulsions may have a caloric density tailored to the nutritional needs of the ultimate user, although in most instances the emulsions comprise generally at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz (740-810 kcal/liter) formulas are more commonly used in preterm or low birth weight infants, and the 20-21 kcal/fl oz (675-680 to 700 kcal/liter) formulas are more often used in term infants. In some embodiments, the emulsion may have a caloric density of from about 100 kcal/liter to about 660 kcal/liter, including from about 150 kcal/liter to about 500 kcal/liter.

In certain embodiments, the formula is a human milk fortifier, including a concentrated human milk fortifier. Human milk or other infant formula, after fortification with a concentrated liquid human milk fortifier, will most typically have a caloric density ranging from about 19 kcal/fl oz (0.64 kcal/ml) to about 26.7 kcal/fl oz (0.9 kcal/ml), with the 22-25 kcal/fl oz formulations (0.74-0.84 kcal/ml) being more useful in preterm infants, and the 19-21 kcal/fl oz (0.64-0.71 kcal/ml) formulations more useful for term infants.

Concentrated liquid human milk fortifiers are generally formulated to have a caloric density of at least about 1.25 kcal/ml (37 kcal/fl oz), including from about 1.4 kcal/ml (42 kcal/ft oz) to about 5 kcal/ml (149 kcal/fl oz), and also including from about 1.5 kcal/ml (44 kcal/fl oz) to about 2.5 kcal/ml (74 kcal/fl oz), and also including from about 1.9 kcal/ml (56 kcal/fl oz) to about 2.0 kcal/ml (59 kcal/fl oz).

Nutritional Powders

The nutritional powders include powders in the form of flowable or substantially flowable particulate compositions, or at least particulate compositions. Particularly suitable nutritional powder forms include spray dried, agglomerated or dryblended powder compositions, or combinations thereof, or powders prepared by other suitable methods. The compositions can easily be scooped and measured with a spoon or similar other device, wherein the compositions may easily be reconstituted with a suitable aqueous liquid, typically water, to form a nutritional liquid, such as an infant formula, for immediate oral or enteral use. In this context, "immediate" use generally means within about 48 hours, most typically within about 24 hours, preferably right after or within 20 minutes of reconstitution.

While not wishing to be bound by theory, it is believed that administration of nutritional compositions in accordance with the general inventive concepts inhibits DPPIV, either directly or otherwise, thereby leading to an increase in GLP-2. This results in enhanced or improved circulation which provides better blood flow and nutrient and oxygen delivery to the targeted areas (e.g., the brain), allowing the targeted areas to mature more readily. Thus, improved or enhanced blood flow reduces inflammation and neural cell death, thereby allowing for catch-up maturation of the infant's brain.

Nutritional compositions according to the present disclosure include a protein with a degree of hydrolysis (DH) of 10% to 75%, at least one of a monoglyceride, free fatty acids, salts of free fatty acids, cholesterol, and a phospholipid. In certain exemplary embodiments, the nutritional compositions comprise a protein with a degree of hydrolysis of 10% to 75%, a phospholipid, cholesterol, and at least one of a monoglyceride, a free fatty acid, a salt of a free fatty acid. In certain exemplary embodiments, the nutritional compositions comprise a protein with a degree of hydrolysis of 10% to 75%, soy lecithin, cholesterol, and monoglycerol palmitate.

Hydrolyzed Protein

The various embodiments of the nutritional compositions described herein preferably include a protein with a degree of hydrolysis (DH) of 10% to 75%. In certain exemplary embodiments, the nutritional compositions include a protein with a DH of 10% to 55%. In certain exemplary embodiments, the nutritional compositions include a protein with a DH of 15% to 70%. In certain exemplary embodiments, the nutritional compositions include a protein with a DH of 20% to 65%. In certain exemplary embodiments, the nutritional compositions include a protein with a DH of 25% to 60%. In certain exemplary embodiments, the nutritional compositions include a protein with a DH of 25% to 55%.

In certain exemplary embodiments, the nutritional compositions include at least about 0.1 grams of hydrolyzed protein per liter of nutritional composition, including at least about 1 g/liter to about 150 g/liter, including at least about 1 g/liter to about 80 g/liter and including at least about 5 g/liter about 50 g/liter. In certain exemplary embodiments, the hydrolyzed protein makes up substantially all of the protein component of the nutritional composition. In certain exemplary embodiments, the hydrolyzed protein is present in an amount of 1% to 75% by weight of the total protein, including amount of 3% to 50% by weight of the total protein. In certain exemplary embodiments, the hydrolyzed protein is present in an amount of 3% to 40% by weight of the total protein. In certain exemplary embodiments, the hydrolyzed protein is present in an amount of 3% to 30% by weight of the total protein. In certain exemplary embodiments, the hydrolyzed protein is present in an amount of 3% to 20% by weight of the total protein. In certain exemplary embodiments, the hydrolyzed protein is present in an amount of 3% to 10% by weight of the total protein. In certain exemplary embodiments, the hydrolyzed protein is present in an amount of 5% to 10% by weight of the total protein. In certain exemplary embodiments, the hydrolyzed protein is present in an amount of 5% to 50% by weight of the total protein. In certain exemplary embodiments, the hydrolyzed protein is present in an amount of 10% to 50% by weight of the total protein. In certain exemplary embodiments, the hydrolyzed protein is present in an amount of 20% to 50% by weight of the total protein. In certain exemplary embodiments, the hydrolyzed protein is present in an amount of 30% to 50% by weight of the total protein. In certain exemplary embodiments, the hydrolyzed protein is present in an amount of 40% to 50% by weight of the total protein. In certain exemplary embodiments, the hydrolyzed protein is present in an amount of 50% to 75% by weight of the total protein. In certain exemplary embodiments, the hydrolyzed protein is present in an amount of 50% to 90% by weight of the total protein. In certain exemplary embodiments, the hydrolyzed protein is present in an amount of 50% to 100% by weight of the total protein.

The hydrolyzed protein may be present in the nutritional composition in these or other amounts, so long as the amount used is effective in improving blood flow to the brain. The hydrolyzed proteins may be derived from any suitable source. In some embodiments, the hydrolyzed proteins are derived from casein, whey, soy, pea, rice, corn, wheat, canola, potato, collagen, etc.

The amount of protein with DH of 10% to 75% that is effective for use according to the disclosed methods may vary based on the age or nutritional needs of the particular individual. In certain exemplary embodiments, the amount of protein with DH of 10% to 75% that is effective in, for example, improving blood flow to the brain, may be determined in an animal model (such as that described in more detail below) or in an in vitro assay.

The hydrolyzed proteins according to the disclosed embodiments may be included as a portion of the protein in various infant nutritional compositions including preterm formulas, term formulas, human milk fortifiers, high protein formulas, concentrated liquids, and reconstitutable powders. Non-limiting examples of products that are suitable for inclusion of the hydrolyzed protein according to the general inventive concepts include the Similac and Alimentum lines of infant products sold by Abbott Nutrition.

Predigested Fat

The term "predigested fat" as used herein refers to monoglycerides, free fatty acids, salts of free fatty acids, and combinations thereof.

Monoglycerides

In certain exemplary embodiments, the nutritional compositions of the present disclosure include a fatty acid-containing monoglyceride, also known as a monoacylglycerol, alone or in addition to the fat component as described below. Monoglycerides are normal metabolites in the body formed during the breakdown of triglycerides and diglycerides. As noted, the fatty acid-containing monoglycerides may be included in the nutritional compositions in combination with a fatty acid component, such as fatty acids and/or fatty acid salts as described below, or may be included in the nutritional compositions in the absence of the fatty acid component.

Suitable fatty acid-containing monoglycerides for use in the nutritional compositions may include fatty acids having a chain length of from 4 to 22 carbon atoms, including fatty acids having a chain length of from 14 to 20 carbon atoms, and including palmitic acid (16 carbon atoms). Particularly preferred are monoglycerides wherein at least 70% of the fatty acids in the monoglycerides are at the Sn-1 position (also referred to as the alpha position), including monoglycerol palmitate having at least about 70% of the palmitic acid residues at the Sn-1 position, including at least about 80% of the palmitic acid residues at the Sn-1 position, and including from about 85% to about 100% of the palmitic acid residues at the Sn-1 position. Further, in some embodiments, the monoglycerides included in the nutritional compositions described herein may include trace amounts of diglycerides, free glycerol, and/or free fatty acids. As used herein, the term "trace amounts" means amounts not exceeding 10 wt %, but more commonly less than 7.5 wt %.

In one specific embodiment, the monoglyceride (and optionally the fatty acid component as discussed below) in the nutritional composition are partially or totally provided to the product through the use of hydrolyzed lard, palm oil, or hydrolyzed tallow. Palm oil, lard, tallow, and other animal-based products, can be added to the nutritional composition and hydrolyzed into monoglycerides and fatty acids by pancreatic lipase. Alternatively, the lard or tallow can be hydrolyzed prior to incorporation into the nutritional composition to produce monoglycerides and fatty acids, which can be introduced into the nutritional composition. Palm oil, lard, tallow, or hydrolyzed lard or tallow, can provide a portion or all of the monoglycerides and/or fatty acids in the nutritional composition.

In certain exemplary embodiments, the monoglyceride in the nutritional composition are partially or totally derived from oils such as vegetable oils, marine oils, fish oils, algae oil, fungal oils, tree resin, and combinations thereof. Suitable vegetable oils include, for example, olive oil, canola oil, corn oil, palm oil, soybean oil, and combinations thereof. In certain exemplary embodiments, the monoglycerides are derived from various oils such as soy oil or coconut oil. Particular examples of monoglycerides include monoglycerol palmitate (i.e., glycerol 1-monopalmitate), monoglycerol oleate, monoglycerol linoleate, and combinations thereof.

In certain exemplary embodiments, the nutritional compositions of the present disclosure include a fatty acid-containing monoglyceride in an amount of at least about 10% by weight of the fat component included in the nutritional composition, including at least about 15% by weight of the fat component included in the nutritional composition, including at least about 20% by weight of the fat component included in the nutritional composition, including from 12% to 45%, including from 15% to 25%, and including about 10%, including about 15%, including about 20%, including about 25%, including about 30%, and further including about 35%, or even about 40%, or even about 50%, or even about 60%, or even about 70%, or even about 80%, or even about 90%, or even about 100% by weight of the fat component included in the nutritional composition.

Free Fatty Acid

In certain exemplary embodiments, the nutritional compositions of the present disclosure include a fatty acid component comprising at least one of a free fatty acid and a salt of a free fatty acid as a part of the predigested fat system. Fatty acids are normal metabolites in the body, formed during the breakdown of fat (triglycerides, diglycerides, cholesterol esters, and certain phospholipids). This fatty acid component is separate and distinct from the fatty acid-containing monoglycerides discussed above.

Any fatty acid beneficial in a nutritional composition can be included in the nutritional compositions as part of the fat system. In one embodiment, the fatty acid is an unsaturated free fatty acid. In some embodiments including unsaturated free fatty acids, the total amount of unsaturated free fatty acids with a chain length of longer than 14 carbon atoms is no less than 60 wt %. Exemplary fatty acids suitable for inclusion in the nutritional compositions described herein include, but are not limited to, arachidonic acid, linolenic acid, docosahexaenoic acid, stearidonic acid, oleic acid, eicosenoic acid, mead acid, erucic acid, nervonic acid, and mixtures and combinations thereof. Particularly preferred fatty acids include arachidonic acid, linoleic acid, linolenic acid, docosahexaenoic acid, and oleic acid.

The fatty acid component for inclusion in the predigested fat system include those derived from oils such as vegetable oils, marine oils, fish oils, algae oil, fungal oils, animal fats, fractionated animal fats and combinations thereof. Suitable vegetable oils include, for example, olive oil, canola oil, corn oil, soybean oil, and combinations thereof. In one embodiment, when animal fat is used, the fatty acids are derived by enzymatic hydrolysis of lard or tallow and the level of palmitic and stearic acid in the resultant fatty acid mixture is reduced to less than 20% of the total fatty acids, including less than 2% of the total fatty acids. In another embodiment, at least some of the fatty acids are derived from soybean oil or tree resin. Fatty acids derived from an oil source are substantially free of diglycerides and triglycerides.

Generally, the fatty acids will be derived from a source oil that contains less than about 20% (by weight) palmitic acid and/or stearic acid. In some embodiments the fatty acids will be derived from a source oil that contains less than about 15% (by weight), including less than about 10% (by weight), including less than about 5% (by weight), and including less than 2% (by weight) palmitic acid and/or stearic acid.

In one specific embodiment, the fatty acids are derived from a source oil that contains less than about 20% (by weight), including from about 10% (by weight) to about 15% (by weight) palmitic acid and/or stearic acid and/or myristic acid. In another specific embodiment, the nutritional composition includes palmitic acid in an amount of less than about 10% (by weight) of the total fatty acids.

In certain exemplary embodiments, the nutritional compositions of the present disclosure may include the fatty acids in salt form; that is, the fatty acids may be added into the nutritional compositions as fatty acid salts. In one suitable embodiment, the fatty acids are added to the nutritional composition in the form of calcium fatty acid salts, magnesium fatty acid salts or a combination thereof.

In certain exemplary embodiments, the nutritional compositions of the present disclosure include fatty acids or fatty acid salts in an amount of at least about 10% (by weight) of the fat component included in the nutritional composition, including at least about 15%, including at least about 20%, including from about 10% to about 60%, including from about 15% to about 40%, and including from about 15% to about 35%, including about 10%, including about 15%, including about 20%, including about 25%, including about 30%, including about 35%, and further including about 40%, or even about 50%, or even about 60%, or even about 70%, or even about 80%, or even about 90%, or even about 100% by weight of the fat component included in the nutritional composition. The fatty acids or fatty acid salts may be present in the nutritional composition in these or other amounts, so long as the amount used is effective in enhancing maturation of an infant's brain.

In certain exemplary embodiments, the nutritional compositions of the present disclosure include a mixture of a fatty-acid containing monoglyceride at least one of a free fatty acid and a salt of a free fatty acid. In these embodiments, the nutritional composition contains the mixture in an amount of at least 10% (by weight) of the fat component included in the nutritional composition, including at least about 15%, including at least about 20%, including from about 10% to about 40%, including from about 20% to about 65%, including from about 25% to about 50%, including from about 15% to about 30%, and including from about 15% to about 25%, including about 10%, including about 15%, including about 20%, including about 25%, including about 30%, including about 35%, and further including about 40% or even about 50%, or even about 60%, or even about 70%, or even about 80%, or even about 90%, or even about 100% by weight of the fat component included in the nutritional composition.

Phospholipids

In certain exemplary embodiments, the nutritional compositions of the present disclosure include phospholipids. The amount of phospholipids included in the nutritional compositions can vary based on the particular product or the nutritional needs of the intended consumer. In certain exemplary embodiments, the nutritional compositions include at least about 1.8 grams of phospholipids per liter of nutritional composition, including about 3.6 g/liter to about 12 g/liter, and about 5.4 g/liter to about 6.4 g/liter. In certain exemplary embodiments, the phospholipids are present in an amount of at least about 5% by weight of the fat component, including about 10% to about 30% by weight of the fat component, including amount of about 15% to about 20% by weight of the fat component. The phospholipids may be present in the nutritional composition in these or other amounts, so long as the amount used is effective in enhancing maturation of an infant's brain. The phospholipids may be derived from any suitable source. In some embodiments, the phospholipids are derived from lecithins, including soy lecithin.

While lecithins are used in the art as emulsifiers in liquid food products including nutritional liquids, lecithins are typically added at relatively low amounts in such capacity, typically about 0.5 to 1% of the total fat, so that the liquid products remain homogeneous and do not separate. Where higher levels of lecithins (5% by weight of the oil) are used, emulsions are destabilized, forming two layers—an oil-rich and an oil-depleted layer. Typical commercial soy lecithin contains about 70% phospholipids. Because of these negative properties, lecithins are not typically used at the levels described herein.

Lecithins are predominantly a mixture of glycerol phospholipids (e.g., phosphatidylcholine, phosphatidylethanolamine and phosphatidylinositol). Phosphatidylcholine is typically the major glycerol phospholipid component. Lecithins may also contain other compounds such as free fatty acids, monoglycerides, diglycerides, triglycerides, glycolipids, and other lipid/fatty acid containing compounds. Lecithins are sometimes classified as glycerol phospholipids or phosphotides. This class of compounds has amphiphilic properties and thus emulsifying functionality.

Non-limiting examples of lecithins suitable for use herein include egg lecithin, wheat lecithin, corn lecithin, soy lecithin, modified lecithin, and combinations thereof. Lecithins suitable for use herein may be obtained from any known or otherwise suitable nutrition source. For example, soy lecithin may be obtained from ADM Specialty Food Ingredients, Decatur, Ill., USA, from Solae, LLC, St. Louis, Mo., USA, and from American Lecithin Company, Oxford, Conn., USA.

Cholesterol

In certain exemplary embodiments, the nutritional compositions of the present disclosure include cholesterol. It has been reported that newborn formula fed infants have a negative cholesterol balance due to a high level of fecal excretion of bile components. Thus, formula fed infants need to use the hepatically synthesized cholesterol to manufacture bile. The amount of cholesterol included in the nutritional compositions can vary based on the particular product or the nutritional needs of the intended consumer. In certain exemplary embodiments, the nutritional compositions include at least about 0.05 grams of cholesterol per liter of nutritional composition, including about 0.1 g/liter to about 0.5 g/liter, and about 0.2 g/liter to about 0.3 g/liter. In certain exemplary embodiments, the cholesterol is present in an amount of about 0.1% to about 0.4% by weight of the fat component, including amount of about 0.2% to about 0.3% by weight of the fat component. The cholesterol may be present in the nutritional composition in these or other amounts, so long as the amount used is effective in enhancing maturation of an infant's brain. The cholesterol may be derived from any suitable source.

The nutritional compositions disclosed herein may comprise fat, protein, carbohydrate, minerals and vitamins, all of which are selected in kind and amount to meet the dietary needs of the intended population. For example, an infant formula is made to meet the dietary needs of the intended infant population. Unless otherwise indicated herein, the term "fat" refers to the total fat (i.e., fat component) in the nutritional composition. In other words, the fat system forms at least a portion of the fat of the nutritional composition. In accordance with certain embodiments, the nutritional composition further comprises carbohydrate, fat, and protein, wherein at least a portion of the fat is the fat system.

The nutritional compositions may include any protein, fat, carbohydrate or source thereof that is known for or otherwise suitable for use in an oral nutritional composition, provided that the macronutrient is safe and effective for oral administration to infants and is otherwise compatible with the other ingredients in the infant formula. The protein, fat, and carbohydrate fat can be adjusted as necessary by one skilled in the art based on the disclosure herein to obtain the desired caloric density and protein level.

Although total concentrations or amounts of the protein, carbohydrate, and fat may vary depending upon the product form (e.g., powder or ready-to-feed liquid) and targeted dietary needs of the intended user, such concentrations or amounts most typically fall within one of the embodied ranges described in the following table (each numerical value in the table is preceded by the term "about"), inclusive of any other essential fat, protein, and or carbohydrate ingredients as described herein.

TABLE 1

| Nutrient % Total Cal. | Embodiment A | Embodiment B | Embodiment C |
|---|---|---|---|
| Carbohydrate | 0-98 | 2-96 | 10-75 |
| Protein | 0-98 | 2-96 | 5-70 |
| Fat | 0-98 | 2-96 | 20-85 |
| | Embodiment D | Embodiment E | Embodiment F |
| Carbohydrate | 30-50 | 25-50 | 25-50 |
| Protein | 15-35 | 10-30 | 5-30 |
| Fat | 35-55 | 1-20 | 2-20 |

The nutritional compositions may contain any percentage or amount of protein, fat, and carbohydrate described herein in combination with any disclosed percentage or amount of hydrolyzed proteins and fat system so long as the combination is safe and effective for oral administration to infants. In a particular embodiment, the nutritional composition (as administered) includes an amount of the combination of a protein with DH of 10% to 75%; at least one of monoglycerides, free fatty acids, salts of free fatty acids; a phospholipid; and cholesterol, that is effective in, for example, improving blood flow to an infant's brain, enhancing maturation of an infant's brain, or reducing inflammation and neuronal cell death, or combinations thereof.

Protein

In addition to the hydrolyzed protein discussed above, any known or otherwise suitable protein or protein source may be included in the nutritional compositions of the present disclosure, provided that such proteins are suitable for feeding to infants, and in particular, newborn infants.

Non-limiting examples of suitable protein or sources thereof for use in the infant formulas include hydrolyzed, partially hydrolyzed or non-hydrolyzed proteins or protein sources, which may be derived from any known or otherwise suitable source such as milk (e.g., casein, whey), animal (e.g., meat, fish), cereal (e.g., rice, corn), vegetable (e.g., pea, soy), or combinations thereof. Non-limiting examples of such proteins include milk protein isolates, milk protein concentrates as described herein, casein protein isolates, extensively hydrolyzed casein, whey protein, sodium or calcium caseinates, whole cow milk, partially or completely defatted milk, soy protein isolates, soy protein concentrates, and so forth. The proteins for use herein can also include free amino acids known for use in nutritional compositions, non-limiting examples of which include L-alanine, L-aspartic acid, L-glutamic acid, glycine, L-histidine, L-isoleucine, L-leucine, L-phenylalanine, L-proline, L-serine, L-threonine, L-valine, L-tryptophan, L-glutamine, L-tyrosine, L-methionine, L-cysteine, taurine, L-arginine, L-carnitine, and combinations thereof.

Fat

In addition to the ingredients of the fat system discussed above, any known or otherwise suitable fat or fat source may be included in the nutritional compositions of the present disclosure, provided that such fats are suitable for feeding to infants, and in particular, newborn infants.

Non-limiting examples of suitable fats or sources thereof for use in the infant formulas described herein include coconut oil, fractionated coconut oil, soybean oil, corn oil, olive oil, safflower oil, high oleic safflower oil, high GLA-safflower oil, oleic acids, MCT oil (medium chain triglycerides), sunflower oil, high oleic sunflower oil, structured triglycerides, palm and palm kernel oils, palm olein, canola oil, flaxseed oil, borage oil, evening primrose oil, blackcurrant seed oil, transgenic oil sources, marine oils (e.g., tuna, sardine), fish oils, fungal oils, algae oils, cottonseed oils, and combinations thereof. In one embodiment, suitable fats or sources thereof include oils and oil blends including long chain polyunsaturated fatty acids (LC-PUFAs). Some non-limiting specific polyunsaturated acids for inclusion include, for example, docosahexaenoic acid (DHA), arachidonic acid (ARA), eicosapentaenoic acid (EPA), linoleic acid (LA), and the like. Non-limiting sources of arachidonic acid and docosahexaenoic acid include marine oil, egg derived oils, fungal oil, algal oil, and combinations thereof. Particularly preferred fat sources include high oleic safflower oil, soy oil, and coconut oils, which may all be used in combination with ARA and/or DHA oil. In one preferred embodiment, the infant formula included a combination of high oleic safflower oil, soy oil, and coconut oil, in combination with ARA oil and DHA oil.

Carbohydrate

Carbohydrates suitable for use in the nutritional compositions include any carbohydrates that are compatible with the essential elements and features of the nutritional compositions of the present disclosure, provided that such carbohydrates are suitable for feeding to infants, and in particular, newborn infants.

Non-limiting examples of suitable carbohydrates or sources thereof for use in the infant formulas described herein include maltodextrin, hydrolyzed, intact, or modified starch or cornstarch, glucose polymers, corn syrup, corn syrup solids, rice-derived carbohydrates, rice syrup, pea-derived carbohydrates, potato-derived carbohydrates, tapioca, sucrose, glucose, fructose, lactose, high fructose corn syrup, honey, sugar alcohols (e.g., maltitol, erythritol, sorbitol), artificial sweeteners (e.g., sucralose, acesulfame potassium, stevia), indigestible oligosaccharides such as fructooligosaccharides (FOS), and combinations thereof. In one embodiment, the carbohydrate includes a maltodextrin having a DE value of less than 20.

Optional Ingredients

The nutritional compositions of the present disclosure include nutritional compositions which include other optional ingredients that may modify the physical, chemical, aesthetic or processing characteristics of the products or serve as pharmaceutical or additional nutritional components when used in the targeted population. Many such optional ingredients are known or otherwise suitable for use in medical food or other nutritional compositions or pharmaceutical dosage forms and may also be used in the compositions herein, provided that such optional ingredients are safe for oral administration and are compatible with the essential and other ingredients in the selected product form.

Non-limiting examples of such optional ingredients include preservatives, anti-oxidants, emulsifying agents, buffers, fructooligosaccharides, galactooligosaccharides, human milk oligosaccharides and other prebiotics, pharmaceutical actives, additional nutrients as described herein, colorants, flavors, thickening agents and stabilizers, lubricants, and so forth, and combinations thereof.

A flowing agent or anti-caking agent may be included in the powder formulas as described herein to retard clumping or caking of the powder over time and to make a powder embodiment flow easily from its container. Any known flowing or anti-caking agents that are known or otherwise suitable for use in a nutritional powder or product form are suitable for use herein, non limiting examples of which include tricalcium phosphate, silicates, and combinations thereof. The concentration of the flowing agent or anti-caking agent in the nutritional composition varies depending upon the product form, the other selected ingredients, the desired flow properties, and so forth, but most typically range from about 0.1% to about 4%, including from about 0.5% to about 2%, by weight of the composition.

A stabilizer may also be included in the nutritional compositions. Any stabilizer that is known or otherwise suitable for use in a nutritional composition is also suitable for use herein, some non-limiting examples of which include gums such as modified starches, gellan gum, carrageenan, and xanthan gum. The stabilizer may represent from about 0.1% to about 5.0%, including from about 0.5% to about 3%, including from about 0.7% to about 1.5%, by weight of the infant formula.

Methods of Manufacture

The nutritional compositions of the present disclosure may be prepared by any known or otherwise effective manufacturing technique for preparing the selected product solid or liquid form. Many such techniques are known for any given product form such as nutritional liquids or powders and can easily be applied by one of ordinary skill in the art to the infant formulas described herein.

The nutritional compositions of the present disclosure can therefore be prepared by any of a variety of known or otherwise effective formulation or manufacturing methods.

In one suitable manufacturing process, for example, at least two separate slurries are prepared. The two slurries are later blended together, heat treated, standardized, and either terminally sterilized to form a retort infant formula or aseptically processed and filled to form an aseptic infant formula. Alternately, the slurries can be blended together, heat treated, standardized, heat treated a second time, evaporated to remove water, and spray dried to form a powder infant formula.

The slurries formed may include a carbohydrate-mineral (CHO-MIN) slurry, a protein-water slurry (PIW), and a protein-in-fat (PIF) slurry. Initially, the CHO-MIN slurry is formed by dissolving selected carbohydrates (e.g., lactose, galactooligosaccharides, etc.) in heated water with agitation, followed by the addition of minerals (e.g., potassium citrate, magnesium chloride, potassium chloride, sodium chloride, choline chloride, etc.). Soy lecithin is then added to the CHO-MIN slurry. The resulting CHO-MIN slurry is held with continued heat and moderate agitation until it is later blended with the other prepared slurries. The PIF slurry is formed by heating and mixing the oil (e.g., high oleic safflower oil, soybean oil, coconut oil, monoglycerides, etc.) and emulsifier (e.g., soy lecithin), and then adding oil soluble vitamins, mixed carotenoids, protein (e.g., milk protein concentrate, milk protein hydrolysate, etc.), carrageenan (if any), calcium carbonate or tricalcium phosphate (if any), and ARA oil and DHA oil (in some embodiments) with continued heat and agitation. The resulting PIF slurry is held with continued heat and moderate agitation until it is later blended with the other prepared slurries. PIW is with the CHO-MIN slurry, and the PIF slurry is added under adequate agitation. The pH of the resulting blend is adjusted to 6.6-7.0, and the blend was held under moderate heated agitation. ARA oil and DHA oil is added at this stage in some embodiments. The ratio blends is assembled by blending target amounts of PIW, PIF and CHO/MIN, the blend is then heated and homogenized. Water soluble vitamins are added and the standardized ratio is either spray dried or diluted, filled in appropriate containers, then retorted.

The composition is then subjected to high-temperature short-time (HTST) processing, during which the composition is heat treated, emulsified and homogenized, and then cooled. Water soluble vitamins, any trace minerals and ascorbic acid are added, the pH is adjusted to the desired range if necessary, flavors (if any) are added, and water is added to achieve the desired total solid level. For aseptic infant formulas, the emulsion receives a second heat treatment through an aseptic processor, is cooled, and then aseptically packaged into suitable containers. For retort infant formulas, the emulsion is packaged into suitable containers and terminally sterilized. In some embodiments, the emulsions are heat-treated then spray dried to make a reconstitutable powder. This powder product can be agglomerated or dry blended with other heat labile nutrients.

The spray dried powder nutritional composition or dry-mixed powder nutritional composition may be prepared by any collection of known or otherwise effective techniques, suitable for making and formulating a nutritional powder. For example, when the powder infant formula is a spray-dried nutritional powder, the spray drying step may likewise include any spray drying technique that is known for or otherwise suitable for use in the production of nutritional powders. Many different spray drying methods and techniques are known for use in the nutrition field, all of which are suitable for use in the manufacture of the spray dried powder infant formulas herein. Following drying, the finished powder may be packaged into suitable containers.

Methods of Use

The nutritional compositions of the present disclosure include infant formulas and human milk fortifiers that are orally administered to infants, including preterm or term infants. The infant formulas may be administered as a source of nutrition for infants, to enhance blood flow to the brain and/or to enhance maturation of the brain, or both. Generally, an increase or improvement in blood flow will improve maturation of an organ (e.g., brain), especially in those in need of catch-up growth. One subclass of the general infant population that can effectively utilize the infant formulas described herein include those infants that are susceptible to, or at a risk of (at an elevated risk as compared to the general infant population) immaturity of the central nervous system, including the brain. These infants who are susceptible to or at risk of having immaturity of, for example, the brain are herein referred to as "in need of" assistance (or "in need thereof" as referring to the assistance needed) in combating organ development problems such as neural inflammation and neural cell death.

Based on the forgoing, because some of the method embodiments of the present disclosure are directed to specific subsets or subclasses of infants (that is, the subset or subclass of infants that are "in need" of assistance in addressing infant formula tolerance or respiratory issues) in those embodiments, not all infants can benefit from all method embodiments described herein as not all infants will fall within the subset or subclass of infants as described herein.

The infant formulas will typically be administered daily, at intake volumes suitable for the age of the infant. For instance, in certain exemplary embodiments, the methods of the present disclosure include methods of administering one or more of the formulas of the present disclosure to an infant at the average intake volumes described herein. In other embodiments, newborn infants are provided with increasing formula volumes during the initial weeks of life. Such volumes most typically range to up to about 100 mL/day on average during the first day or so of life; up to about 200 to about 700 mL/day, including from about 200 to about 600 mL/day, and also including from about 250 to about 500 mL/day, on average during the remainder of the three month newborn feeding period. It is to be understood, however, that such volumes can vary considerably depending upon the particular newborn infant and their unique nutritional needs during the initial weeks or months of life, as well as the specific nutrients and caloric density of the infant formula administered.

In certain exemplary embodiments, the methods of the present disclosure are directed to infants during the initial days, weeks or months of life. Desirably, in certain exemplary embodiments, the infant formulas described herein are administered to the infant for a duration of at least the first week of life, more desirably during at least the first two weeks of life, more desirably during at least the first one or two months of life, more desirably during at least the first four months of life, and more desirably during at least the first six months of life, and including up to the first year of life. Thereafter, the infant may be switched to a conventional infant formula, alone or in combination with human milk. It should be understood by one skilled in the art based on the disclosure herein that the infant formulas described herein can be used alone, or in combination with human breast milk, or in combination with other infant formulas.

The nutritional compositions used in the methods described herein, unless otherwise specified, are infant formulas (including human milk fortifiers) and may be in any product form, including ready-to-feed liquids, concentrated liquids, reconstituted powders, and the like as described above. In embodiments where the infant formulas are in powder form, the method may further comprise reconstituting the powder with an aqueous vehicle, most typically water or human milk, to form the desired caloric density, which is then orally or enterally fed to the infant. The powdered formulas are reconstituted with a sufficient quantity of water or other suitable fluid such as human milk to produce the desired caloric density, as well as the desired feeding volume suitable for one infant feeding. The infant formulas may also be sterilized prior to use through retort or aseptic means.

In certain exemplary embodiments, the present disclosure is directed to a method of enhancing maturation of an infant's brain (including therapeutic or prophylactic treatments). Enhanced maturation is intended to refer generally to a rate commensurate with catch-up maturation and does not necessarily refer to a rate of maturation that is greater than what would be expected for a normal term infant (i.e., one that is not in need of catch-up growth/maturation). Thus, in certain exemplary embodiments, enhanced maturation refers to maturation at a rate that is less than or equal to what would be expected for a term infant, but is greater than that of an otherwise untreated preterm infant. The method comprises administering to the infant one or more of the infant formulas of the present disclosure. In certain exemplary embodiments, the infant to whom the formula is administered is a newborn infant, including a preterm infant. In certain exemplary embodiments, the infant to whom the formula is administered has experienced, or is at risk of experiencing diminished or impeded maturation of the brain.

In certain exemplary embodiments, the present disclosure is directed to a method for the prevention, delay of progression, or the treatment of a circulatory disorder characterized by inadequate blood flow to the brain. The method comprises administering to an individual in need thereof a nutritional composition comprising a therapeutically effective amount of a DPP-IV inhibiting protein wherein the protein has a degree of hydrolysis of 10% to 75%. In certain exemplary embodiments, the infant to whom the formula is administered is a newborn infant, including a preterm infant. In certain exemplary embodiments, the infant to whom the formula is administered has experienced, or is at risk of experiencing inadequate blood flow to the brain.

In certain exemplary embodiments, administration of the nutritional compositions according to the general inventive concepts provides increased blood flow and nutrient distribution to the individual. In particular, administration of hydrolyzed proteins according to the general inventive concepts results in inhibition of DPP-IV. This increases the level of GLP-2, resulting in increased blood flow to certain organs, including the brain. In addition, neuronal tissue inflammation may be treated or alleviated by the administration the nutritional compositions according to the claims. The increased blood flow and reduction in neuronal tissue inflammation may also lead to the prevention, delay of progression, or the treatment of a neurodegenerative disorder.

In certain exemplary embodiments, improved maturation of the brain in an individual, and particularly, an infant, is identified by measuring the amount of a biomarker associated with brain cell apoptosis. The biomarker may be measured in a model organism following administration of a nutritional composition disclosed herein to the model organism. The model organism can be any known model organism for measuring these properties. In some embodiments, the model organism is a rodent, and, in particular, a mouse.

EXAMPLES

The following examples illustrate specific embodiments and/or features of the infant formulas and methods of the present disclosure. The examples are given solely for the purpose of illustration and are not to be construed as limitations of the present disclosure, as many variations thereof are possible without departing from the spirit and scope of the disclosure. Unless otherwise specified, the retort sterilized formulas, which may be prepared in accordance with the manufacturing methods described herein, are ready-to-feed liquid formulas. All exemplified amounts are weight percentages based upon the total weight of the composition, unless otherwise specified.

Whey protein concentrate was suspended 14.6 g/L in 0.025 M TRIS (pH 8.0). Pancreatin (Sigma P-7545) prepared at 6 g/L in 0.025M TRIS (pH 8.0), was added in a WPC volume to Pancreatin volume ratio of 9:1. The suspension was incubated at 37° C. for between 0 and 240 minutes. The protein hydrolysates were then tested for molecular weight (MW) and average peptide length. The results are listed in table 2 below.

TABLE 2

| Pancreatin digestion time, minutes | MW median of Protein Hydrolysate (Daltons) | Average peptide chain length (amino acids) | DPP-IV inhibition, % of control |
| --- | --- | --- | --- |
| 0 | 10,767 | 90 | 4 |
| 15 | 1813 | 15 | 68 |
| 30 | 1217 | 10 | 74 |
| 60 | 803 | 6.7 | 77 |
| 90 | 693 | 5.8 | 78 |
| 120 | 637 | 5.3 | 79 |
| 240 | 539 | 4.5 | 81 |

Figure 2:
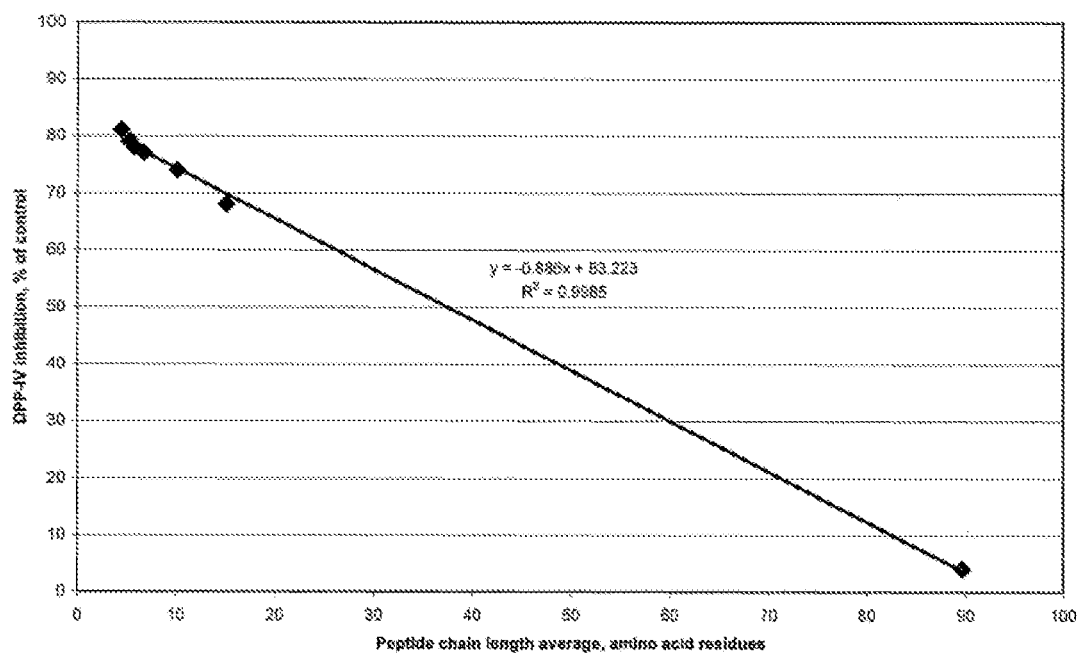
FIG. 2 shows the results of DPP-IV inhibition as a function of average peptide chain length for several exemplary proteins.
Figure 3:
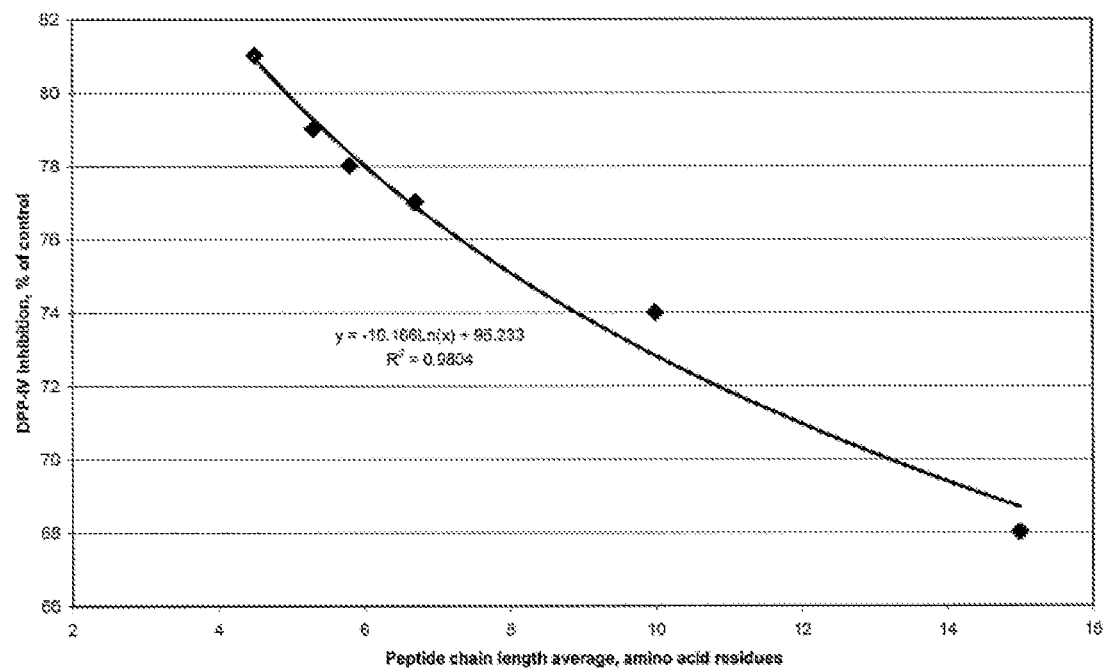
FIG. 3 shows the results of DPP-IV inhibition as a function of average peptide chain length for several exemplary proteins.

FIG. 1 shows the results of DPP-IV inhibition as a function of molecular weight (as measured by HPLC determination of the DPP-IV substrate Gly-Pro-p-nitroanilide and amount of p-nitroaniline released before and after hydrolysis of DPP-IV). FIG. 2 shows the results of DPP-IV inhibition as a function of average peptide chain length for several exemplary hydrolyzed proteins. FIG. 3 shows the results of DPP-IV inhibition as a function of average peptide chain length for a subset of the hydrolyzed proteins.

Table 3 is a bill of material for a Modified Nutritional composition (HMF-M-PDF) including hydrolyzed protein and a fat system in accordance with the general inventive concepts.

TABLE 3

| Ingredients | Amount per 1000 lbs | UOM |
| --- | --- | --- |
| Maltodextrin | 125.3 | lb |
| Casein Hydrolysate | 114.3 | lb |
| Soy Fatty Acids | 23.5 | lb |
| Modified Corn Starch | 12.0 | lb |
| Soy Lecithin | 11.7 | lb |
| Calcium Phospahte | 11.1 | lb |
| Potassium Citrate | 7.1 | lb |
| Ascorbic acid | 4.4 | lb |
| Magnesium Chloride | 3.5 | lb |
| Calcium Hydroxide | 3.3 | lb |
| Monoglycerides | 2.9 | lb |

TABLE 3-continued

| Ingredients | Amount per 1000 lbs | UOM |
|---|---|---|
| Arachidonic Acid | 2.5 | lb |
| Docosahexaenoic Acid | 2.1 | lb |
| Potassium Chloride | 1.5 | lb |
| Water soluble vitamin mineral premix | 600.0 | g |
| Sodium Chloride | 353.0 | g |
| Mixed carotenoids | 230.0 | g |
| Cholesterol | 192.1 | g |
| Vitamin ADEK premix | 176.4 | g |
| Choline Chloride | 133.0 | g |
| Gellan Gum | 99.8 | g |
| Potassium hydroxide | as needed | |
| Ingredient Water | as needed | |

Necrotizing enterocolitis was induced in mice pups by supplementation of feed with enteric bacteria made from a stock created from a specimen obtained from an infant with surgical NEC. A mixture of a 2 to 1 blend of model infant formula (Abbott Nutrition) and Esbilac (PetAg) canine milk replacer supplemented with enteric bacteria stock from an infant with surgical NEC (12.5 µl original stool slurry in 1 ml formula) via gavage five times/day. The seven to ten day old mice pups were divided into 4 groups. Group 1 (DR) was dam reared; Group 2 was fed a control composition including the NEC formula (NEC-F); Group 3 was fed a modified NEC formula (HMF-M) with hydrolyzed protein as described herein; Group 4 was fed a modified NEC formula including hydrolyzed protein and a fat system (HMF-M-PDF) according to the disclosed embodiments. The mice received hypoxia (5% $O_2$, 95% $N_2$) for 10 minutes in a hypoxic chamber (Billups-Rothenberg) twice daily for 4 days. Animals were fed 50 µl per gram of mouse body weight using a 24-French angiocatheter that was placed into the mouse esophagus under direct vision.

Table 4 is a comparison of the fat components

TABLE 4

| | HMF-M | HMF-M-PDF |
|---|---|---|
| Fat System (% fat) | Soy Oil (86.5) | Soy Fatty Acids (53.3) |
| | ARA (5.8) | MDG (6.7) |
| | DHA (5.7) | Soy Lecithin (26.6) |
| | VIT ADEK (0.9) | Cholesterol (1.1) |
| | Carotenoids (1.2) | ARA (5.8) |
| | MDG (1) | DHA (5.7) |
| | | VIT ADEK (0.9) |
| | | Carotenoids (1.2) |
| Protein (100%) | Casein hydrolysate | Casein hydrolysate |

Figure 4:
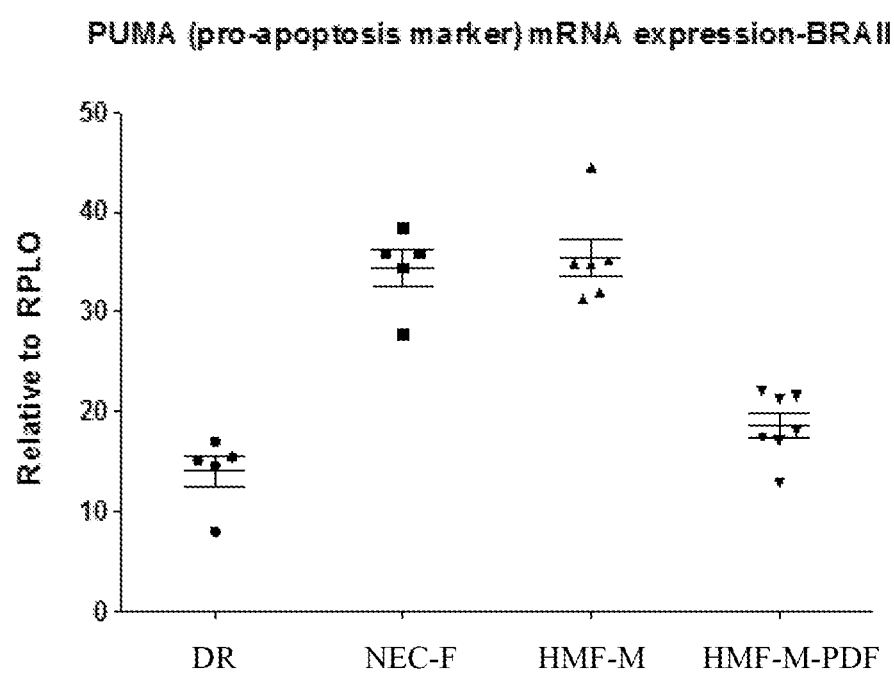
FIG. 4 shows the amount of PUMA (a proaptosis marker) mRNA expression as determined after administration of various nutritional compositions to hypoxia treated newborn mice.
Figure 5:
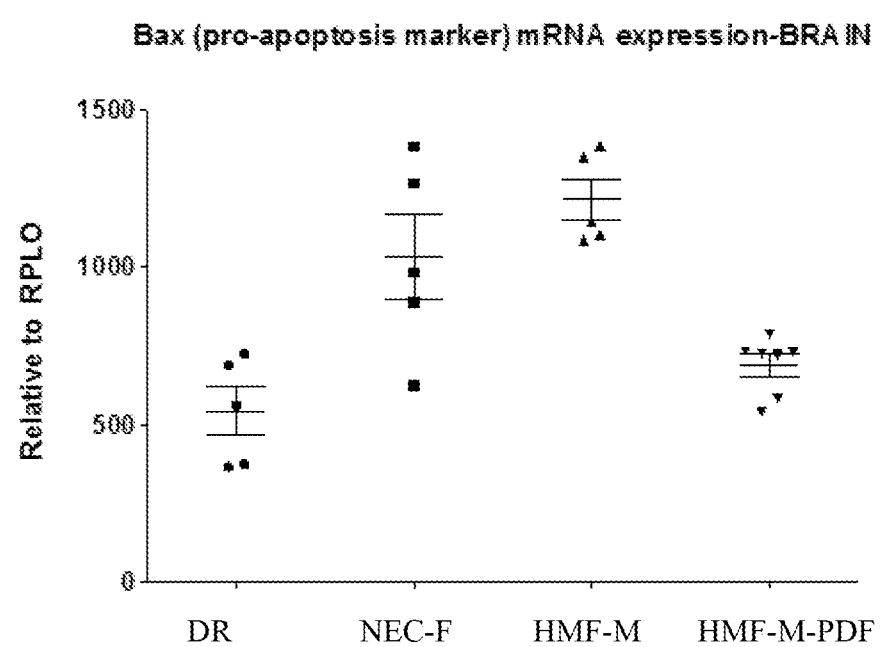
FIG. 5 shows the amount of BAX (a proaptosis marker) mRNA expression as determined after administration of various nutritional compositions to hypoxia treated newborn mice.

FIG. 4 shows the amount of PUMA (a proaptosis marker) mRNA expression relative to housekeeping gene RPLO as determined by real time PCR after administration of various nutritional compositions to mice. FIG. 5 shows the amount of BAX (a proaptosis marker) mRNA expression relative to housekeeping gene RPLO as determined by real time PCR after administration of various formulas to mice. Feeding hypoxia treated new born mice a formula containing hydrolyzed protein and a fat system according to the disclosed embodiments reduces cell apoptosis as evidenced by the measured levels of PUMA and BAX.

Figure 6:
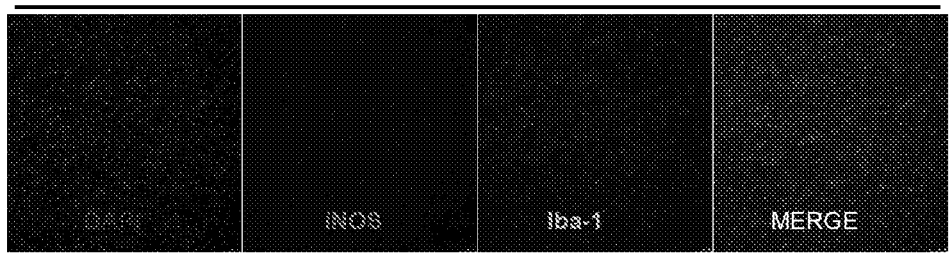
FIG. 6 shows brain inflammation data on hypoxia treated mice that were dam reared (BM) or that were administered a NEC-F formula.
Figure 6:
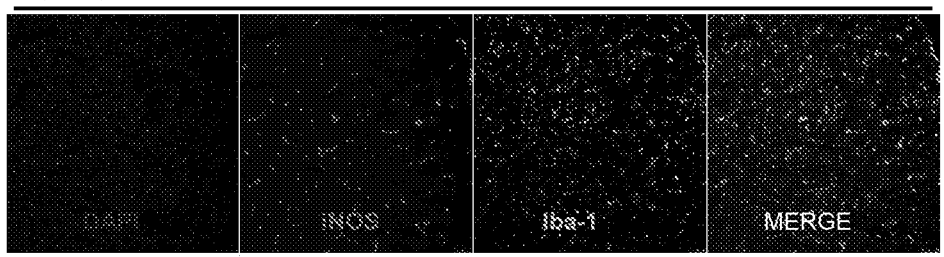
Figure 7:
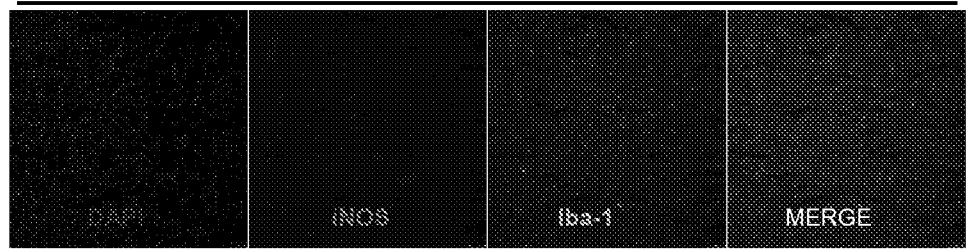
FIG. 7 shows the results of brain inflammation data on hypoxia treated mice obtained after administration of a modified nutritional composition (HMF-M) and a modified nutritional composition also including a predigested fat system (HMF-M-PDF).
Figure 7:
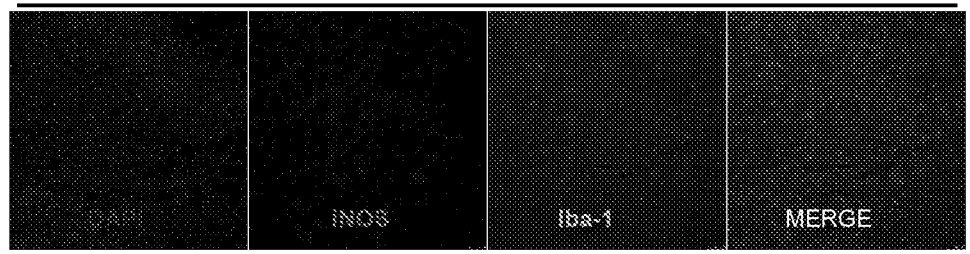

FIG. 6 and FIG. 7 show the results of administration of the various nutritional compositions to hypoxia treated new born mice. As can be seen from the data, feeding a formula containing both protein having a degree of hydrolysis of 10% to 75% and a fat system (PDF—soy lecithin, cholesterol, monoglycerol palmitate and at least one of a free fatty acid from soy and a salt of a free fatty acid from soy) according to the present disclosure reduces brain cell apoptosis. As can be seen from the data, adding HMF-M and HMF+PDF to NEC formula reduced the number of iNOS and Iba-1 expressing cells in the hypoxia-treated pups brains, which indicates a lower level of oxidative stress and inflammation. While not wishing to be bound by theory, it is Applicants' belief that such reduction in brain cell apoptosis promotes brain development. It is hypothesized that the GLP-2 levels are increased upon administration of the combination of hydrolyzed protein and PDF in the nutritional composition. This administration eventually leads to a better blood flow. Enhanced blood flow stimulates brain development via increasing supply of nutrients and reduced inflammation.

Although the present disclosure has been described with reference to specific embodiments, it should be understood that the limitations of the described embodiments are provided merely for purpose of illustration and are not intended to limit the present invention and associated general inventive concepts. Instead, the scope of the present invention is defined by the appended claims, and all variations and equivalents that fall within the range of the claims are intended to be embraced therein. Thus, other embodiments than the specific exemplary ones described herein are equally possible within the scope of these appended claims.

The various embodiments of the nutritional compositions of the present disclosure may also be substantially free of any optional or selected essential ingredient or feature described herein, provided that the remaining infant formulas still contain all of the required ingredients or features as described herein. In this context, and unless otherwise specified, the term "substantially free" means that the selected infant formulas contain less than a functional amount of the optional ingredient, typically less than 1%, including less than 0.5%, including less than 0.1%, and also including zero percent, by weight of such optional or selected essential ingredient.

The nutritional compositions and methods of the present disclosure may comprise, consist of, or consist essentially of the essential elements of the products and methods as described herein, as well as any additional or optional element described herein or otherwise useful in nutritional infant formula applications or other applications.

To the extent that the terms "includes," "including," "contains," or "containing" are used in the specification or the claims, they are intended to be inclusive in a manner similar to the term "comprising" as that term is interpreted when employed as a transitional word in a claim. Furthermore, to the extent that the term "or" is employed (e.g., A or B) it is intended to mean "A or B or both." When Applicants intend to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto."

What is claimed is:

1. A method of inhibiting neuronal cell death in an infant in need thereof, the method comprising administering to the infant a nutritional composition consisting essentially of a casein protein with a degree of hydrolysis of 10% to 75% and a mixture of a monoglycerol palmitate, soy lecithin, cholesterol, and at least one of a free fatty acid from soy and a salt of a free fatty acid from soy, and wherein after administration the infant's neuronal cell death is reduced.

2. The method of claim 1, wherein the infant in need thereof is a preterm infant.

3. The method of claim 1, wherein the nutritional composition is a human milk fortifier.

4. The method of claim 1, wherein the nutritional composition is a powdered human milk fortifier.

5. The method of claim 1, wherein the nutritional composition is an infant formula.

6. The method of claim 5, wherein the nutritional composition is a preterm infant formula.

7. The method of claim 1, wherein the nutritional composition further comprises a carbohydrate.

8. A method of treating neuronal tissue inflammation in an infant in need thereof, the method comprising administering to the infant a nutritional composition consisting essentially of a casein protein with a degree of hydrolysis of 10% to 75% and a mixture of a monoglycerol palmitate, soy lecithin, cholesterol, and at least one of a free fatty acid from soy and a salt of a free fatty acid from soy, and wherein after administration the infant's neuronal tissue inflammation is reduced.

9. The method of claim 8, wherein the nutritional composition is a human milk fortifier.

10. The method of claim 9, wherein the nutritional composition is a powdered human milk fortifier.

11. The method of claim 8, wherein the nutritional composition is an infant formula.

12. The method of claim 11, wherein the nutritional composition is a preterm infant formula.

13. A method of reducing neuronal tissue inflammation in an infant in need thereof, the method comprising administering to the infant a nutritional composition consisting essentially of a casein protein with a degree of hydrolysis of 10% to 75% and a mixture of a monoglycerol palmitate, soy lecithin, cholesterol, and at least one of a free fatty acid from soy and a salt of a free fatty acid from soy.

* * * * *